(12) United States Patent
Scheuerman et al.

(10) Patent No.: US 6,426,357 B1
(45) Date of Patent: Jul. 30, 2002

(54) ANTAGONISTS OF FOLLICLE STIMULATING HORMONE ACTIVITY

(75) Inventors: Randall A. Scheuerman, Santa Clara; Stephen D. Yanofsky, Palo Alto; Christopher P. Holmes, Saratoga; Derek MacLean, Mountain View; Beatrice Ruhland, Los Altos; Ronald W. Barrett, Saratoga, all of CA (US); Jay E. Wrobel, Lawrenceville; Ariamala Gopalsamy, Mahwah, both of NJ (US)

(73) Assignee: Affymax, Inc., Palo Alto, CA (US)

( * ) Notice: Subject to any disclaimer, the term of this patent is extended or adjusted under 35 U.S.C. 154(b) by 0 days.

(21) Appl. No.: 09/629,180

(22) Filed: Jul. 31, 2000

Related U.S. Application Data
(60) Provisional application No. 60/145,828, filed on Jul. 27, 1999.

(51) Int. Cl.⁷ .................... A61K 31/427; C07D 277/04
(52) U.S. Cl. ................. 514/369; 548/182; 548/187
(58) Field of Search ...................... 514/342, 369, 514/397, 445; 548/182, 187; 549/59, 77

(56) References Cited

U.S. PATENT DOCUMENTS
5,032,588 A * 7/1991 Brooks et al.

\* cited by examiner

*Primary Examiner*—Floyd D. Higel
*Assistant Examiner*—Sonya N. Wright
(74) *Attorney, Agent, or Firm*—Brobeck, Phleger & Harrison LLP

(57) ABSTRACT

The present invention provides a compound of the formula:

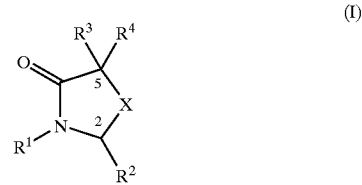

(I)

and methods for using the same, wherein $R^1$, $R^2$, $R^3$, $R^4$ and X are those defined herein.

13 Claims, No Drawings

ANTAGONISTS OF FOLLICLE STIMULATING HORMONE ACTIVITY

CROSS-REFERENCE TO RELATED APPLICATIONS

This application claims benefit of U.S. Provisional Patent Application Ser. No. 60/145,828, filed Jul. 27, 1999, the disclosure of which is incorporated herein by reference for all purposes.

FIELD OF THE INVENTION

This invention relates broadly to novel thiazolidinones. More specifically, the invention relates to thiazolidinones which modulate Follicle Stimulating Hormone (FSH) activity.

BACKGROUND OF THE INVENTION

Approximately 400,000 germ cells are stored in the ovaries of the human female at the time of puberty. No further germ cells are made. Beginning at the time of puberty and ending at menopause, there are approximately 400 ovulatory menstrual cycles which consume essentially all of the germ cells in the human ovary. About 1,000 germ cells are consumed in each menstrual period. However, in any one menstrual cycle, only one germ cell, developed in what becomes the dominant follicle, is ovulated and available for pregnancy.

Although the details are not accurately known, the mechanism by which a single egg is selected each month to become the dominant egg is dependent upon a complex interaction between one or more hormones from the ovary, hypothalamus and the pituitary. Three glycoprotein hormones (luteinizing hormone (LH), follicle stimulating hormone (FSH) and chorionic gonadotropin (hCG)) act on the ovary to stimulate steroid synthesis and secretion. LH and FSH are secreted by the pituitary and together play a central role in regulating the menstrual cycle and ovulation. hCG is secreted by the developing placenta from the early stages of pregnancy and its role is to maintain steroid secretion by the corpus luteum, which is necessary to prevent ovulation during pregnancy.

In the normal cycle, there is a mid-cycle surge in LH concentration which is followed by ovulation. An elevated estrogen level, which is brought about by the endogenous secretion of LH and FSH, is required for the LH surge to occur. The estrogen mediates a positive feedback mechanism which results in the increased LH secretion.

Oral contraceptive agents have been used by over 200 million women worldwide and by 1 of 4 women in the United States under the age of 45. Such agents are popular because of ease of administration, low pregnancy rate (less than 1 percent) and a relatively low incidence of side effects. Typically, oral contraceptives inhibit ovulation by suppressing FSH and LH secretion. As a consequence, the secretion of all ovarian steroids is also suppressed, including estrogen, progesterone and androgen. These agents also exert minor direct inhibitory effects on the reproductive tract, altering the cervical mucus, thereby decreasing sperm penetration and decreasing the motility and secretions of the fallopian tubes and uterus.

Thiazolidinones are a class of small molecule organic compounds which have found limited pharmaceutical use. For example, thiazolidinones have been found to have central nervous system activity. See, for example, Tripathi, et al., "Thiazolidinone congeners as central nervous system active agents." *Arzneimittelforschung* 43:632–5 (1993). CNS activities which have been identified include, for example, antipsychotic properties. See, Mutlib, et al., "Metabolism of an atypical antipsychotic agent, 3-[4-[4-(6-fluorobenzo[b]thien-3-yl)-1-piperazinyl]butyl]-2,5,5-trimethyl-4-thiazolidinone (HP236)." *Drug Metab. Dispos.* 24:1139–50 (1996). Other thiazolidinones have been found to be CNS antiischemic agents. See, Ruterbories, et al., "Pharmacokinetics of a novel butylated hydroxytoluene-thiazolidinone CNS antiischemic agent LY256548 in rats, mice, dogs and monkeys." *Drag Metab. Dispos.* 18:674–9 (1990). Thiazolidinones have also been used as antimicrobial agents. See, for example, Ley, et al., "Inhibition of multiplication of Mycobacterium leprae by several antithyroid drugs." *Am. Rev. Respir. Dis.* 111:651–5 (1975).

The synthesis of novel thiazolidinones offers the promise for discovering new pharmaceutical agents with applications in areas as diverse as, for example, antimicrobial therapy and the treatment of strokes with CNS antiischemic agents. Of particular interest is the use of novel thiazolidinones as regulators of mammalian fertility.

Although a number of oral contraceptives are commercially available, there still remains a need for new fertility-regulating agents which are useful for both in vivo and in vitro applications. A class of small molecule FSH receptor antagonist compounds which are inexpensive to prepare, easily purified, easily administered and which exhibit a broad range of activities would represent a significant advance in the field of oral contraceptive agents. Quite surprisingly, the present invention provides such small molecule thiazolidinone FSH receptor antagonists.

SUMMARY OF THE INVENTION

The present invention provides a class of novel thiazolidinones possessing a range of pharmaceutical applications and activities. Thus, in one aspect, the present invention provides novel thiazolidinones having the formula:

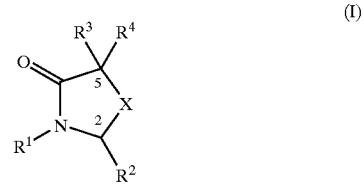

wherein, $R^1$ is a member selected from the group consisting of aryl and substituted aryl, alkyl and substituted alkyl;

$R^2$ is a member selected from the group consisting of heterocyclic and substituted heterocylic groups;

$R^3$ and $R^4$ are independently members selected from the group including hydrogen and —$(CH_2)_m CONR^5R^6$;

$R^5$ and $R^6$ are independently members selected from the group consisting of hydrogen, alkyl, substituted alkyl, cycloalkyl, substituted cycloalkyl, arylalkyl, substituted arylalkyl, heterocyclicalkyl and substituted heterocyclicalkyl groups;

X is a member selected from the group consisting of S, S=O, and O=S=O;

m is a number from 0 to 3.

In a second aspect, the present invention provides novel thiazolidinones

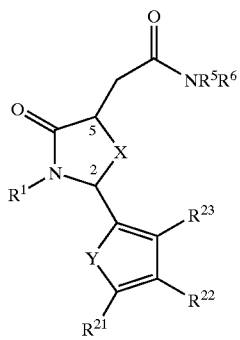

(III)

wherein, $R^1$ is a member selected from the group consisting of aryl and substituted aryl alkyl and substituted alkyl;

$R^{21}$, $R^{22}$, and $R^{23}$ are members independently selected from the group consisting of H, halogen, lower alkyl, substituted lower alkyl, lower alkoxy, substituted lower alkoxy, phenyl, substituted phenyl, aryloxy, substituted aryloxy, alkynyl, substituted alkynyl and nitro groups. Preferred aryloxy groups are phenoxy and benzyloxy and preferred substituted aryloxy groups are substituted phenoxy and substituted benzyloxy.

Y is a member selected from the group consisting of —O—, —S— and $NR^{24}$ wherein $R^{24}$ is H or lower alkyl.

$R^5$ and $R^6$ are independently members selected from the group consisting of hydrogen, alkyl, substituted alkyl, cycloalkyl, substituted cycloalkyl, arylalkyl, substituted arylalkyl, heterocyclicalkyl and substituted heterocyclicalkyl groups; and X is a member selected from the group consisting of S, S═O, and O═S═O.

In another aspect, the invention provides a class of FSH receptor antagonists, wherein the receptor antagonists are noncompetitve with FSH for the receptor FSH binding site.

In yet another aspect, the invention provides a class of compounds that modulate FSH hormone activity, the compounds having: (a) a molecular weight of from about 200 daltons to about 1000 daltons; and (b) an FSH antagonist activity corresponding to an $IC_{50}$ standard of no more than 25 μM, preferably no more than 11 μM; wherein the antagonist activity of this class of compounds to the FSH receptor is competitively inhibited by a compound described above.

In a preferred embodiment, this class of compounds has a molecular weight of about 300 daltons to about 800 daltons. In another preferred embodiment, this class of compounds has an FSH receptor antagonist activity, as expressed by an $IC_{50}$ standard, of no more than 11 μM.

In still another aspect, the invention provides methods of using the compounds, i.e., thiazolidinones, for diverse pharmaceutical applications including, for example, CNS anti-ischemic agents, agents with antipsychotic or other psychoactive properties, antimicrobial agents and mammalian fertility regulating agents. When used as mammalian fertility regulating agents, the thiazolidinones are preferably antagonists of the FSH receptor.

As such, in another aspect, the present invention provides pharmaceutical compositions which contain one or more of the compounds of the invention in conjunction with pharmaceutically acceptable excipients, carriers, diluents, etc. The pharmaceutical compositions can also contain agents which are themselves pharmacologically active and which serve to enhance, supplement, decrease or otherwise regulate the pharmacological effect of the pharmaceutical compositions.

Other features, objects and advantages of the invention and its preferred embodiments will become apparent from the detailed description which follows.

DETAILED DESCRIPTION OF THE INVENTION AND PREFERRED EMBODIMENTS

A. Abbreviations and Definitions

HATU, [O-(7-Azabenzotriazol-1-yl)-1,1,3,3-tetramethyl-uroniumhexafluorophosphate]; DIEA, diisopropylethylamine; FMOC, fluorenylmethoxycarbonyl; DECP, diethyl cyanophosphonate; DCM, dichloromethane; DBU, 1,8-diazabicyclo[5.4.0]undec-7-ene; CHO, chinese hamster ovary; RBF, round-bottomed flask.

The term "independently selected" is used herein to indicate that the R groups, e.g., $R^1$, $R^2$, and $R^3$, can be identical or different (e.g., $R^1$, $R^2$ and $R^3$ may all be substituted alkyls or $R^1$ and $R^2$ may be a substituted alkyl and $R^3$ may be an aryl, etc.).

A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical having from 1–12 carbons and preferably, from 1–6 carbons. When "lower alkyl" is used, it refers to an alkyl group which has from 1–6 carbons. Suitable alkyl radicals include, for example, methyl, ethyl, n-propyl, i-propyl, 2-propenyl (or allyl), n-butyl, t-butyl (or 2-methylpropyl), etc.

"Substituted alkyl" refers to alkyl as just described including one or more functional groups such as lower alkyl, aryl, acyl, halogen, (i.e., alkylhalos, e.g., $CF_3$), hydroxy, nitro, cyano, amino, alkoxy, alkylamino, acylamino, acyloxy, aryloxy, aryloxyalkyl, mercapto, carboxylic acid, carboxylic acid derivatives, carboxylic acid amides, sulfonic acids, sulfonic acid derivatives, both saturated and unsaturated cyclic hydrocarbons, heterocycles and the like. These groups may be attached to any carbon of the alkyl moiety.

The term "aryl" is used herein to refer to an aromatic substituent having a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others.

"Substituted aryl" refers to aryl as just described including one or more functional groups such as lower alkyl, acyl, halogen, alkylhalos (e.g., $CF_3$), hydroxy, nitro, cyano, amino, alkoxy, alkylamino, acylamino, acyloxy, mercapto, carboxylic acid amide, sulfonic acid amide and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "arylalkyl" is used herein to refer to a subset of "aryl" in which the aryl group is attached through an alkyl group as defined herein. Examples include, but are not limited to, benzyl, phenylethyl and phenylpropyl groups.

"Substituted arylalkyl" defines a subset of "arylalkyl" wherein the aryl moiety of the arylalkyl group is substituted as defined herein for aryl groups.

The term "halogen" is used herein to refer to fluorine, bromine, chlorine and iodine atoms.

The term "hydroxy" is used herein to refer to the group —OH.

The term "amino" is used herein to refer to the group-NRR', where R and R' may independently be hydrogen, lower alkyl, substituted lower alkyl, aryl, substituted aryl or acyl.

The term "alkoxy" is used herein to refer to the —OR group, where R is a lower alkyl or substituted lower alkyl, wherein the alkyl and substituted lower alkyl groups are as described herein. Suitable alkoxy radicals include, for example, methoxy, ethoxy, t-butoxy, etc.

The term "aryloxy" is used herein to refer to the —OR group, wherein R is an aryl, substituted aryl, arylalkyl or substituted arylalkyl as described above. Examples include phenoxy, benzyloxy, phenethyloxy and substituted derivatives thereof.

The term "alkylamino" denotes secondary and tertiary amines wherein the alkyl groups may be either the same or different and may consist of straight or branches, saturated or unsaturated hydrocarbons.

The term "heterocyclic" is used herein to describe a monovalent group having a single ring or multiple condensed rings from 1–12 carbon atoms and from 1–4 heteroatoms selected from nitrogen, sulfur or oxygen within the ring. Heterocyclic groups include saturated, unsaturated, and aromatic ring systems. Such heterocycles include, for example, tetrahydrofuran, morpholine, piperidine, pyrrolidine, thiophene, pyridine, isoxazole, phthalimide, pyrazole, indole, furan, benzo-fused analogs of these rings, etc.

The term "substituted heterocyclic" as used herein describes a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylmino, acylamino, acyloxy, mercapto, etc.

The term "heterocyclicalkyl" is used herein to refer to a subset of "heterocylic" in which the hetetocylcic group is attached through an alkyl group as defined herein.

"Substituted heterocyclicalkyl" defines a subset of "heterocyclicalkyl" wherein the heterocyclic moiety of the hetemocyclicalkyl group is substituted as defined herein for heterocyclic groups.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid and organic acids such as, for example, methanesulfonic acid, ethanesulfonic acid, p-toluenesulfonic acid, salicylic acid and the like. Pharmaceutically acceptable salts include, for example, alkali metal salts, such as sodium and potassium, alkaline earth salts and ammonium salts.

The term "contacting" is used herein interchangeably with the following: combined with, added to, mixed with, passed over, incubated with, flowed over, etc. Moreover, the thiazolidinone compounds of present invention can be "administered" to a subject by any conventional method such as, for example, parenteral, oral, topical and inhalation routes as described herein.

"An amount sufficient" or "an effective amount" is that amount of a given thiazolidinone analog which exhibits the binding/activity of interest or, which provides an improvement in gamete recruitment.

"$IC_{50}$" is the inhibitory concentration: the concentration of a compound at which 50% of the maximal response of that obtained with FSH is inhibited.

"Non-competitive" refers to the nature of the agonist activity exhibited by the compounds of the invention, wherein the compounds act as agonists of and activate the FSH receptor without substantially reducing the magnitude of binding of FSH to the receptor. "Magnitude of binding" refers to the amount of FSH bound by a receptor population and/or the strength of the binding interaction between FSH and the FSH receptor.

The present invention is directed to novel thiazolidinone compounds which exhibit a range of pharmaceutical activities. In a presently preferred embodiment, the novel compounds are small molecule FSH receptor antagonists. These compounds offer numerous advantages over the current state of the art. For example, the compounds of the instant invention are inexpensive and both easily prepared and purified. Further, the compounds exhibit a range of activity regarding the FSH receptor. Such a manifold of compounds of differing activity provides an opportunity to the clinician to modulate the desired level of fertility induction by judicious choice of the fertility-inhibiting agent. In addition, the novel thiazolidinones, as small molecules, exhibit a pharmacokinetic profile which is distinct from that of conventional peptidic hormone preparations. The pharmacokinetic profile can be further modified by judicious choice of the route of administration and manipulating the nature of the substituents on the thiazolidinone nucleus.

As such, in a first aspect, the present invention provides novel thiazolidinones having the formula:

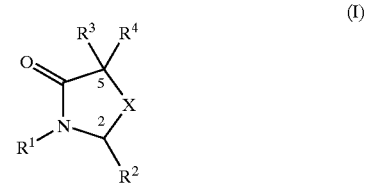

(I)

wherein, $R^1$ is a member selected from the group consisting of aryl and substituted aryl, alkyl and substituted alkyl;

$R^2$ is a member selected from the group consisting of heterocyclic and substituted heterocylic groups;

$R^3$ and $R^4$ are independently members selected from the group including hydrogen and —$(CH_2)_m CONR^5 R^6$;

$R^5$ and $R^6$ are independently members selected from the group consisting of hydrogen, alkyl, substituted alkyl, cycloalkyl, substituted cycloalkyl, arylalkyl, substituted arylalkyl, heterocyclicalkyl and substituted heterocyclicalkyl groups;

X is a member selected from the group consisting of S, S=O, and O=S=O;

m is a number from 0 to 3.

A more preferred embodiment of Formula (I), are novel thiazolidinones of Formula (III)

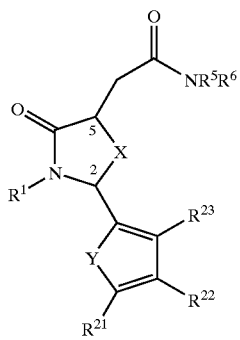

wherein,
- $R^1$ is a member selected from the group consisting of aryl and substituted aryl alkyl and substituted alkyl;
- $R^{21}$, $R^{22}$, and $R^{23}$ are members independently selected from the group consisting of H, halogen, lower alkyl, substituted lower alkyl, lower alkoxy, substituted lower alkoxy, phenyl, substituted phenyl, aryloxy, substituted aryloxy, alkynyl, substituted alkynyl and nitro groups. Preferred aryloxy groups are phenoxy and benzyloxy and preferred substituted aryloxy groups are substituted phenoxy and substituted benzyloxy.
- Y is a member selected from the group consisting of —O—, —S— and $NR^{24}$ wherein $R^{24}$ is H or lower alkyl
- $R^5$ and $R^6$ are independently members selected from the group consisting of hydrogen, alkyl, substituted alkyl, cycloalkyl, substituted cycloalkyl, arylalkyl, substituted arylalkyl, heterocyclicalkyl and substituted heterocyclicalkyl groups; and
- X is a member selected from the group consisting of S, S=O, and O=S=O.

In yet a further preferred embodiment, the present invention provides a compound wherein, when substituent $R^4$, on C-5, is H, and a second substituent at C-5 ($R^3$) is not H, said substituent $R^3$ on C-5 and substituent $R^2$ on C-2 are oriented in a cis manner.

In certain presently preferred embodiments, $R^{21}$, $R^{22}$ and $R^{23}$ are independently chosen from hydrogen and the groups according to Formulae (VIII):

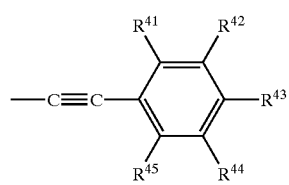

wherein $R^{41}$, $R^{42}$, $R^{43}$, $R^{44}$ and $R^{45}$ are members independently selected from the group consisting of hydrogen, halogen, nitro and trifluoromethyl.

Due to the chiral carbons at positions 2 and 5 (i.e., C-2 and C-5) of the thiazolidinone ring structure, the compounds of the invention can exist in a number of different isomeric and stereoisomeric forms. The configuration of C-2 and C-5 can be such that their substituents are in either a cis or traits configuration. In preferred embodiments, the compounds exist in the cis configuration. Additionally, the combination of absolute configurations available to C-2 and C-5 can take any one of four permutations. Thus, the thiazolidinone nucleus can be 2S, 5S; 2R, 5R; 2S, SR; or 2R, 5S. Presently preferred embodiments are those in which the configuration at C-2 and C-5 are 2S, 5R.

The compounds of the present invention can be used for diverse pharmaceutical applications including, for example, CNS antiischemic agents, agents with antipsychotic or other psychoactive properties, antimicrobial agents and mammalian fertility regulating agents. When used as mammalian fertility regulating agents, the thiazolidinones are preferably antagonists of the FSH receptor.

Examples of the thiazolidinone compounds of the present invention are displayed below. In a preferred embodiment, the $IC_{50}$ values of the compounds having antagonist activity are less than 25 μM. In a more preferred embodiment, the $IC_{50}$ values of the compounds having antagonist activity are less than 11 μM.

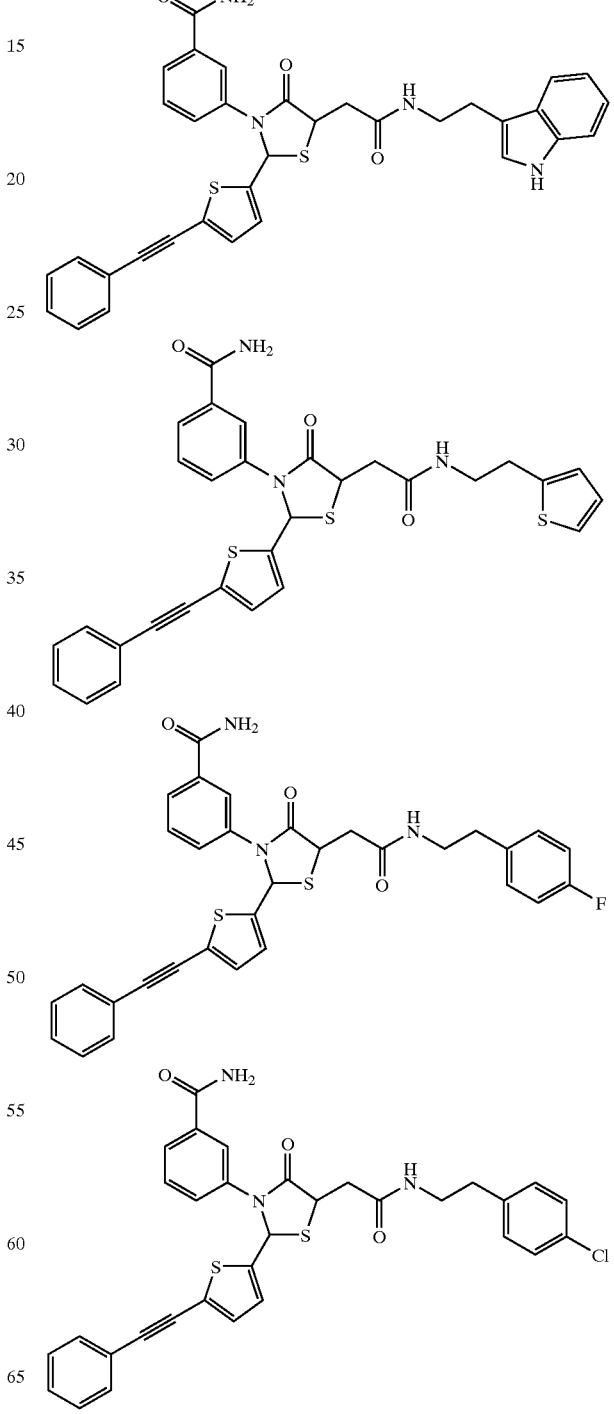

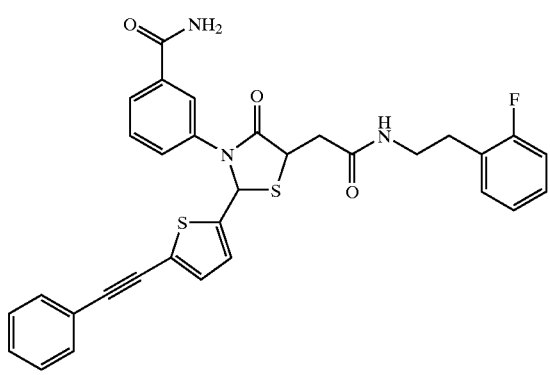
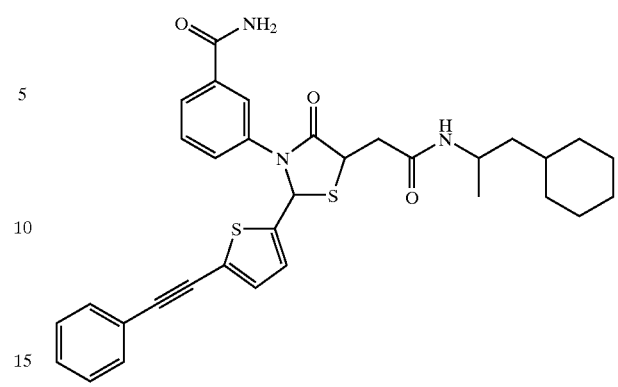
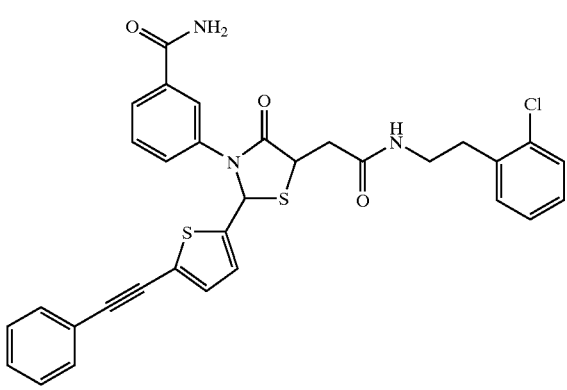
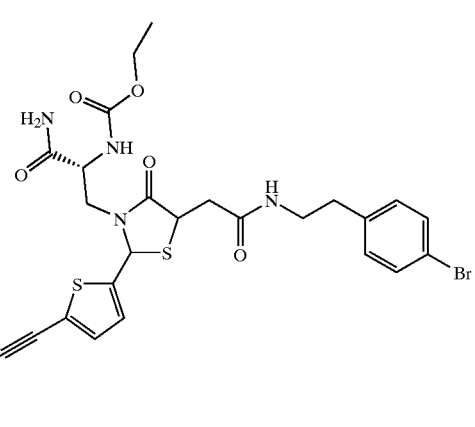
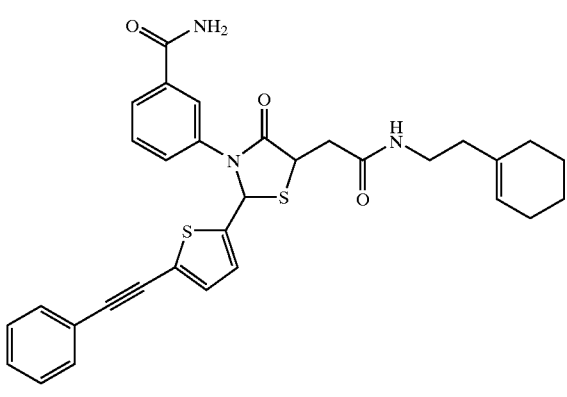
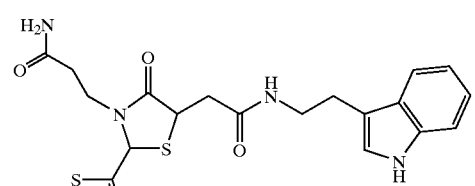
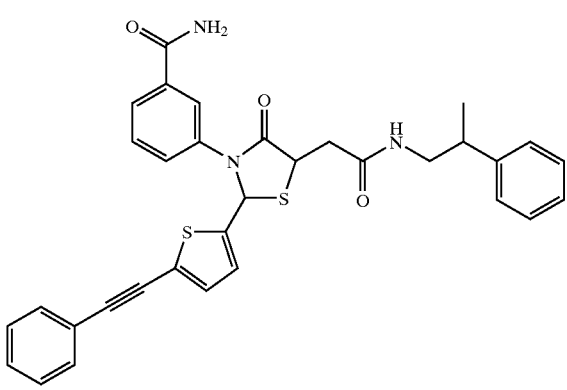
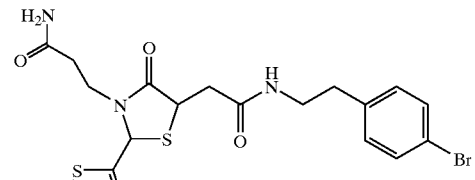

-continued

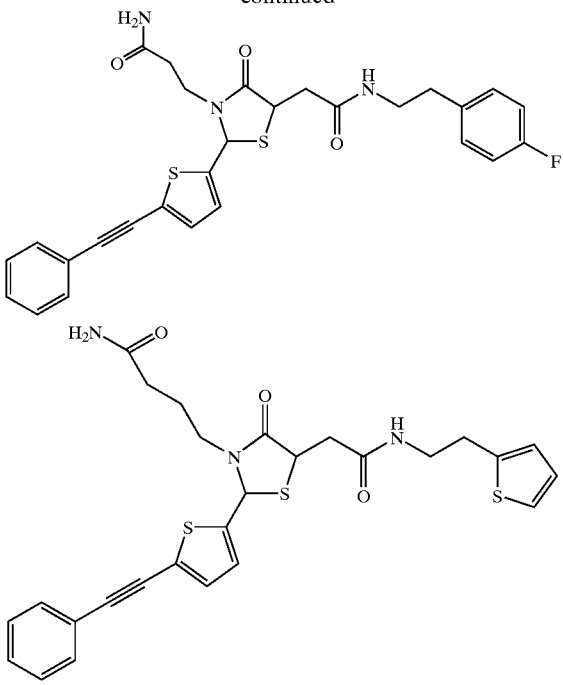

In another aspect, the invention provides a class of FSH receptor antagonists, wherein the receptor antagonist activity is noncompetitve with FSH. In a preferred embodiment, the non-competitive FSH antagonists are organic molecules with a molecular weight of from about 200 daltons to about 1000 daltons. In another preferred embodiment, the invention provides for pharmaceutical formulations containing a FSH receptor antagonist which is non-competitive with FSH. In this aspect, the invention provides regulators of mammalian fertility which are useful in the diverse applications described herein for the thiazolidinones of the invention.

B. Pharmaceutical Compositions and Uses

In another embodiment, the present invention provides pharmaceutical compositions which contain one or more of the compounds of the invention in conjunction with pharmaceutically acceptable excipients, carriers, diluents, etc. The pharmaceutical compositions can also contain other agents which are themselves pharmacologically active and which serve to enhance, supplement, decrease or otherwise regulate the pharmacological effect of the pharmaceutical compositions.

The compounds, i.e., thiazolidinones, of the present invention can be administered to a mammal, e.g., a human patient, alone, in the form of a pharmaceutically acceptable salt, or in the form of a pharmaceutical composition where the compound is mixed with suitable carriers or excipient(s) in a therapeutically effective amount. Further, the compounds and compositions of the invention can be administered to induce menses; to treat endometriosis; to treat dysmenorrhea; to treat endocrine hormone-dependent tumors; to treat uterine fibroids; to inhibit uterine endometrial proliferation; to induce labor; for hormone therapy; and for contraception in both the female and male.

More particularly, the compounds of the present invention are of particular value in the control of hormonal irregularities in the menstrual cycle, for controlling endometriosis and dysmenorrhea, and for inducing menses. In addition, the compounds of the present invention can be used as a method of providing hormone therapy either alone or in combination with estrogenic substances in postmenopausal women, or in women whose ovarian hormone production is otherwise compromised.

Moreover, the compounds of the present invention can be used for control of fertility during the whole of the reproductive cycle. For long-term contraception, the compounds of the present invention can be administered either continuously or periodically depending on the dose. In addition, the compounds of the present invention are of particular value as postcoital contraceptives, for rendering the uterus inimical to implantation, and as "once a month" contraceptive agents. They can be used in conjunction with prostaglandins, oxytocics and the like.

A further important utility for the compounds of the present invention lies in their ability to slow down growth of hormone-dependent cancers. Such cancers include kidney, breast, endometrial, ovarian cancers, and prostate cancer which are characterized by possessing progesterone receptors and can be expected to respond to the products of this invention. Other utilities of the compounds of the present invention include the treatment of fibrocystic disease of the breast and uterine.

By analogy to the demonstrated efficacy of gonadotrophins on the Sertoli cell, that is, the male equivalent of the ovarian granulosa cells, the compounds and compositions of the present invention can be used for male, as well as female, contraception. See, for example, Reichert, et al., "The follicle stimulating hormone (FSH) receptor in testis: interaction with FSH, mechanism of signal transduction, and properties of the purified receptor," Biol. Reprod. 40:13–26 (1989), the disclosure of which is incorporated herein by reference.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example, via injection of the compound directly into an ovary, often in a depot or sustained release formulation. In addition, the compounds can be administered in a targeted drug delivery system, for example, in a liposome coated with an organ surface receptor-specific antibody. Such liposomes will be targeted to and taken up selectively by the organ.

In pharmaceutical dosage forms, the compounds may be administered in the form of their pharmaceutically acceptable salts, or they may also be used alone or in appropriate association, as well as in combination with other pharmaceutically active compounds. In the interest of brevity, the discussion which follows is based on the use of the compounds of the invention as contraceptive agents. That pharmaceutical compositions containing the novel thiazolidinones are useful in other applications, and are not limited to use as contraceptive agents will be apparent to those of skill in the art. In these further applications, adjuncts which serve a purpose analogous to those discussed below (i.e., enhance or supplement the thiazolidinone therapeutic activity) can be included within the formulation.

The thiazolidinone analogs of the present invention can be administered alone, in combination with each other, or they can be used in combination with other known compounds (e.g., contraceptive agent). A number of suitable formulations for use in the present invention are found in *Remington's Pharmaceutical Sciences* (Mack Publishing Company, Philadelphia, Pa., 17th ed. (1985), which is incorporated herein by reference. Moreover, for a brief review of methods for drug delivery, .ee, Langer, *Science* 249:1527–1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the invention, a therapeutically effective dose can be estimated initially from cell culture assays. For example, a dose can be formulated in animal models to achieve a circulating concentration range that includes the $EC_{50}$ as determined in cell culture. Such information can be used to more accurately determine useful doses in humans. Initial dosages can also be estimated from in vitro or in vivo data.

Initial dosages can also be formulated by comparing the effectiveness of the compounds described herein in cell culture assays with the effectiveness of known drugs. For instance, when used as contraceptive agents, initial dosages can be formulated by comparing the effectiveness of the compounds described herein in cell culture assays with the effectiveness of known contraceptive agents. In this method, an initial dosage can be obtained by multiplying the ratio of effective concentrations obtained in cell culture assay for the compound of the present invention and a known contraceptive drug by the effective dosage of the known contraceptive drug. For example, if a compound of the present invention is twice as effective in cell culture assay as the known contraceptive agent (i.e., the $IC_{50}$ of that compound is equal to one-half the $IC_{50}$ of the known contraceptive agent in the same assay), an initial effective dosage of the compound of the present invention would be one-half the known dosage for the known contraceptive agent. Using these initial guidelines one having ordinary skill in the art could determine an effective dosage in humans or other mammals.

Moreover, toxicity and therapeutic efficacy of the compounds described herein can be determined by standard pharmaceutical procedures in cell cultures or experimental animals, e.g., by determining the $LD_{50}$ (the dose required to cause death in 50% of the subjects tested) and the $ED_{50}$ (the dose that produces a defined effect in 50% of the subjects tested). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is appropriate for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, for example, Fingl, et al., In: *The Pharmacological Basis of Therapeutics*, Ch. 1, p. 1 (1975).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

When used as contraceptive agents in the female, the compositions of the invention can be evaluated for their effectiveness by any of a number of art accepted parameters including number of follicles, number of oocytes, number of transferrable embryos, number of pregnancies, the total dose administered and the treatment length. Similarly accepted criteria are available for evaluating the safety of a contraceptive agent. When used as contraceptive agents in the male, effectiveness can be adduced by decreased sperm count, sperm motility and the like. Additional criteria and methods for assessing the efficacy of a thiazolidinone-containing pharmaceutical composition, when used as a contraceptive agent or for another purpose, will be apparent to those of skill in the art.

The thiazolidinones can be incorporated into the pharmaceutical formulation as mixtures of diastereomers, mixtures of enantiomers or as stereochemically distinct compounds. The origin of the isomerism is the chirality of the carbons at positions 2 and 5 of the thiazolidinone ring structure (Formula I). For example in one preferred embodiment, the thiazolidinone component of the pharmaceutical composition is a mixture of cis and trans isomers. In another preferred embodiment, the mixture of cis and trans isomers is enriched in the cis isomer relative to the trans isomer. In a further preferred embodiment, the thiazolidinone is present as the substantially pure cis isomer.

The stereochemistry of the carbon atoms at positions 2 and 5 of the ring is yet another feature of the thiazolidinone constituent which can be varied. In a preferred embodiment, the thiazolidinone constituent is a mixture of the 2S, 5R and 5S, 2R isomers. In a more preferred embodiment, the thiazolidinone constituent is enriched in the 2S, 5R isomer. In still further preferred embodiments, the thiazolidinone constituent is substantially pure 2S, 5R.

In addition to the foregoing, the compounds of the invention are useful in vitro as unique tools for understanding the biological role of FSH, including the evaluation of the many factors thought to influence, and be influenced by, the production of FSH and the interaction of FSH with the FSH-R (e.g., the mechanism of FSH signal transduction/receptor activation). The present compounds are also useful in the development of other compounds that interact with the FSH-R, because the present compounds provide important structure-activity relationship (SAR) information that facilitate that development.

Compounds of the present invention that bind to the FSH receptor can be used as reagents for detecting FSH receptors on living cells, fixed cells, in biological fluids, in tissue homogenates, in purified, natural biological materials, etc. For example, by labelling such compounds, one can identify cells having FSH-R on their surfaces. In addition, based on their ability to bind the FSH receptor, compounds of the present invention can be used in in situ staining, FACS (fluorescence-activated cell sorting), western blotting, ELISA (enzyme-linked immunoadsorptive assay), etc. In addition, based on their ability to bind to the FSH receptor, compounds of the present invention can be used in receptor purification, or in purifying cells expressing FSH receptors on the cell surface (or inside permeabilized cells).

The compounds of the invention can also be utilized as commercial research reagents for various medical research and diagnostic uses. Such uses can include but are not limited to: (1) use as a calibration standard for quantitating the activities of candidate FSH antagonists in a variety of functional assays; (2) use as blocking reagents in random compound screening, i.e., in looking for new families of FSH receptor ligands, the compounds can be used to block recovery of the presently claimed FSH compounds; (3) use in the co-crystallization with FSH receptor, i.e., the compounds of the present invention will allow formation of crystals of the compound bound to the FSH receptor, enabling the determination of receptor/compound structure by x-ray crystallography; (4) other research and diagnostic applications wherein the FSH-receptor is preferably inactivated or such inactivation is conveniently calibrated against a known quantity of an FSH antagonist, and the like; (5) use in assays as probes for determining the expression of FSH receptors on the surface of cells; and (6) developing assays for detecting compounds which bind to the same site as the FSH receptor binding ligands.

The invention will be described in greater detail by way of specific examples.

The following examples are offered for illustrative purposes, and are not intended to limit the invention in any manner. Those of skill in the art will readily recognize a variety of noncritical parameters which can be changed or modified to yield essentially the same results.

EXAMPLE 1

This example details the preparation of optically pure mercaptosuccinic acid and the synthesis of optically pure thiazolidinones from this precursor.

5.1 Synthesis of Optically Pure Mercaptosuccinic Acid a. Preparation of (R)-Bromosuccinic Acid To a 500 mL round bottom flask was added D-aspartic acid ((R)-aspartic acid, 25 g, 188 mmol) and 245 mL of 5 N HBr. The reaction was cooled in an ice bath to 0–5° C., followed by the dropwise addition of sodium nitrite (20.7 g, 301 mmol) in 75 mL of water over five hours. The temperature was maintained below 5° C. during the addition. After the addition was complete, the reaction was allowed to stir for 12 hours at 23–25° C. The reaction was diluted with diethyl ether (120 mL). The aqueous layer was removed and the organic phase was washed with 1 N HCl (100 mL). The combined aqueous phases were washed with EtOAc (100 mL). The combined organic extracts were dried (MgSO$_4$), filtered and concentrated under reduced pressure to leave the product as a slightly yellow solid. The solid was recrystallized from EtOAc (~100 mL) and hexanes (~10 mL) to obtain the product (16.58 g, 84 mmol, 45%) as a white crystalline solid.

b. Preparation of (S)-Bromosuccinic Acid

To a 500 mL round bottom flask was added L-aspartic acid ((S)-aspartic acid, 25 g, 188 mmol) and 245 mL of 5 N HBr. The reaction was cooled in an ice bath to 0–50° C., followed by the dropwise addition of sodium nitrite (20.7 g, 301 mmol) in 75 mL of water over five hours. The temperature was maintained below 50° C. during the addition. After the addition was complete, the reaction was allowed to stir for 12 hours at 23–25° C. The reaction was diluted with diethyl ether (120 mL). The aqueous layer was removed and the organic phase was washed with 1 N HCl (100 mL). The combined aqueous phases were washed with EtOAc (100 ml). The combined organic extracts were dried (MgSO4), filtered and concentrated under reduced pressure to leave the product as a slightly yellow solid. The solid was recrystallized from EtOAc (~100 mL) and hexanes (~10 mL) to obtain the product (19.03 g, 97 mmol, 51%) as a white crystalline solid.

c. Preparation of (S)-Mercaptosuccinic Acid.

To a suspension of sodium thiophosphate dodecahydrate (6 g, 15 mmol) in toluene (50 mL) in an oil bath at 60° C. was added (R)-bromosuccinic acid (0.5 g, 2.5 mmol). The reaction was stirred at 60° C. for 3.5 hours (as the reaction temperature approaches 60° C., the sodium thiophosphate melts forming a biphasic reaction medium). The toluene was then removed under reduced pressure and the resulting white solid was diluted with water (25 mL) and 1 N hydrochloric acid (30 mL), a pH of 1–1.5. The reaction was stirred at 23–25° C. for 1–2 hours, then extracted with EtOAc (3×50 mL). The combined organic extracts were dried over MgSO$_4$, filtered and concentrated to dryness under reduced pressure. The resulting white solid was dissolved in water (3.0 mL) and filtered through a 0.2 μm nylon filter. The filtrate was purified by preparative HPLC (a single injection of 3.0 mL, a Waters PrepPak cartridge Delta-Pak C18 compression column, 15 μm 25×100 mm, 95/5 water/acetonitrile at 12.0 mL/min). The product was collected and lyophilized to afford the product (276 mg, 18.4 mmol, 72.5%) as a white solid.

d. Preparation of (R)-Mercaptosuccinic Acid

To a suspension of sodium thiophosphate dodecahydrate (6 g, 15 mmol) in toluene (50 mL) in an oil bath at 60° C. was added (S)-bromosuccinic acid (0.5 g, 2.5 mmol). The reaction was stirred at 60° C. for 3.5 hours (as the reaction temperature approaches 60° C., the sodium thiophosphate melts forming a biphasic reaction medium). The toluene was then removed under reduced pressure and the resulting white solid was diluted with water (25 mL) and 1 N hydrochloric acid (30 mL), a pH of 1–1.5. The reaction was stirred at 23–25° C. for 1–2 hours, then extracted with EtOAc (3×50 mL). The combined organic extracts were dried over MgSO$_4$, filtered and concentrated to dryness under reduced pressure. The resulting white solid was dissolved in water (3.0 mL) and filtered through a 0.2 μm nylon filter. The filtrate was purified by preparative HPLC (a single injection of 3.0 mL, a Waters PrepPak cartridge Delta-Pak C18 compression column, 15 μm 25×100 mm, 95/5 water/acetonitrile at 12.0 ml/min). The product was collected and lyophilized to afford the product (280 mg, 18.7 mmol. 73.5%) as a white solid.

e. Determination of Enantiomeric Excess (EE)

To a 1 wt % solution of Ná-(2,4-dinitrofluorophenyl)-L-valinamide in acetone (2.0 ml) is added mercaptosuccinic acid (2.0 mg) and 0.5 M NaHCO₃ (1.0 ml). The reaction mixture is heated to 57° C. for 45 minutes. The mixture is removed and diluted with 0.5 N NaHCO₃ (5.0 mL), and washed with ethyl acetate (10 mL). The aqueous phase is acidified with 1 N HCl and extracted with ethyl acetate (5 mL). The adduct is then analyzed by HPLC.

5.2 Synthesis of Optically Pure Thiazolidinones

To a 100 mL peptide vessel was added 2.0 g of Argogel-Rink Amide-FMOC (0.33 mmol/g loading). The resin was washed with dichloromethane (50 mL) and N,N-dimethylformamide (50 mL). The resin was then deprotected with 20% piperidine in N,N-dimethylformamide (50 mL) for 30 minutes. The resin was then washed exhaustively with dichloromethane and N,N-dimethylformamide. 3-Aminobenzoic acid (N-Fmoc protected, 1.0 g, 2.8 mmol) was coupled to the resin with HATU (1.16 g, 3.0 mmol) and DIEA (0.53 mL, 6.0 mmol) in DMF (12 mL) for 16 hours. The resin was then washed exhaustively with dichloromethane and N,N-dimethylformamide. The resin was then deprotected with 20% piperidine in N,N-dimethylformamide (50 mL) for 30 minutes. The resin was then washed exhaustively with dichloromethane and N,N-dimethylformamide.

The resin was split into 2 equal portions and each portion was treated with 10 eq of 4-benzyloxybenzaldehyde and 20 eq. of either R (70% EE) or S (75% EE) mercaptosuccinic. Acetonitrile (5 mL) was added and the reaction was left at RT for 48 hours, then 55° C. for 48 hours. The vessels were cooled and their contents were transferred with THF to a peptide vessel, and washed with hot THF. The resin was then washed exhaustively with dichloromethane and N,N-dimethylformamide.

Each portion was further reacted with 20 eq. of 3,4-dimethoxyphenethylamine, 20 eq. DIEA, and 20 eq. diethylcyanophosphate in DCM for three hours. The resin was washed exhaustively with THF, DMF, DCM, MeOH, DCM in sequence. The products were cleaved with 95% TFA/DCM for 1 hour, drained and washed with DCM (2×2 mL). The solvent was removed under reduced pressure leaving a yellow solid which was purified by preparative HPLC. R-Mercaptosuccinic acid afforded the cis isomer (18 mg, as a 96:4 mixture of 2S,5R:2S,5S). S-Mercaptosuccinic acid afforded the cis isomer (4 mg, as a 55:45 mixture of 2R,5S:2S,5R) and traits isomer (20 mg, as a 55:45 mixture of 2S,5S:2R,5R). The enantiomeric purity was determined on a Pirkle Leucine column employing 65% THF/35% hexane as the eluent at 0.7 ml/min.

EXAMPLE 2

This example details the synthesis of thiophene compounds of the invention.

Into a 250 mL RBF was added 3-aminobenzamide (1.6 g, 11.8 mmol), 5-(phenethynyl)thiophene-2-carboxaldehyde (2.5 g, 11.8 mmol), mercaptosuccinic acid (5.3 g, 35.4 mmol) and acetonitrile (200 mL). The reaction was heated under reflux for 3 days. A white solid had formed. The solid was collected by filtration, and washed with acetonitrile. The solid proved to be the trans isomer (4.0 g, 8.6 mmol, 73%). The filtrate was discarded. The trans isomer was transferred to a 500 mL RBF, with 200 mL THF, and 10 equivalents of DBU. The reaction was heated under reflux, followed by the addition of 20 mL of methanol. The reaction was reflux for 24 hours, cooled, and the solvent removed under reduced pressure. The residue was dissolved in EtOAc (250 mL) and washed with 1 N HCl (2×300 mL). The organic layer was filtered to remove the trans isomer, and then concentrated under reduced pressure. The remaining material was triturated with acetonitrile, filtered, and process repeated to achieve material with 95:5 cistrans ratio. This material was then recrystallized from acetonitrile to afford the cis isomer (>97:3).

Into a 2 mL vial was added the carboxylic acid (25 mg, 0.054 mmol), tryptamine (25 mg) in DMF (0.5 mL), DECP (30 μL), and DIEA (50 μL). The reaction was stirred at room temperature for 24 hours. HPLC analysis showed the reaction to be complete. The material was purified by preparative HPLC (C18 column, 5–95% AcCN/H₂O over 40 minutes, 30 mL/min) to give the cis enantiomers as a white solid (AF21639, 28.0 mg, 0.046 mtnol 86%). HPLC, MS confirm product.

EXAMPLE 3

Example 3 details the preparation of iodobenzyl derivatives of compounds of the invention.

Into a 500 mL was added sulfanilamide (3.71 g, 21.6 mmol) 4-iodobenzaldehyde (5 g, 21.6 mmol), mercaptosuccinic acid (10 g, 64.8 mmol) and acetonitrile (300 mL). The reaction was heated under reflux for 3 days. The reaction was cooled and concentrated under reduced pressure to leave a yellow solid. The solid was dissolved in EtOAc (250 mL) and washed with 1N HCl (2×250 mL), water (3×250 mL), and saturated sodium chloride solution (1×100 mL). The organic layer was separated, dried (MgSO₄), filtered, and concentrated under reduced pressure to leave a yellow solid. The solid was refluxed in chloroform (300 mL), filtered and dried to afford the product (10.5 g, 20.2 mmol, 93%) as a 1:8 ratio of cis:trans enantiomers. HPLC, MS, ¹H NMR, and ¹³C NMR all confirm product.

Into a 500 mL RBF was added the predominately trans acid (5.2 g, 10 mmol). THF (200 mL), DBU (15 mL), and MeOH (50 mL). The reaction was heated under reflux for 48 hours. The reaction was cooled to RT and the solvent was removed under reduced pressure leaving a yellow syrup. The syrup was dissolved in EtOAc (250 mL) and washed with 1N HCl (3×250 mL). The organic layer was concentrated under reduced pressure to leave a yellow solid. The solid was refluxed in chloroform (300 mL), filtered and dried to afford the product (2.25 g, 4.3 mmol, 43%) as a 2;3 ratio of cis:trans enantiomers. HPLC, MS, ¹H NMR, and ¹³C NMR all confirm product.

EXAMPLE 4

Example 4 illustrates the exchange of acetylene for iodine in the compound of Example 3.

Into a 100 mL 3-necked RBF was added the predominately trans acid (5.2 g, 10 mmol), NMP (75 mL), DIEA (51 mmol), and trimethylsilylacetylene (51 mmol). The reaction was deoxygenated by alternating application of vacuum and nitrogen. Tetrakis(triphenylphosphine)palladium(0) (1.156 g, 1 mmol) and copper(I)iodide (760 mg, 4 mmol) were added and the reaction was again deoxygenated. The reaction was stirred under nitrogen at RT for 20 hours. The reaction was diluted with EtOAc (250 mL) and washed with 1N HCl (3×250 mL). The organic layer was concentrated Linder reduced pressure to leave an orange syrup. The syrup was triturated with CHCl₃ (100 mL) to precipitate the product (3.4 g, 7.0 mmol, 70%) as an off-white solid. HPLC, MS, ¹H NMR, and ¹³C NMR all confirm product.

Into a 200 mL RBF containing the carboxylic acid (3.4 g, 7 mmol) was added methanol (100 mL) and potassium carbonate (10 g, 70 mmol). The reaction mixture was stirred at RT for 4 hours. The reaction mixture was diluted with EtOAc (200 mL) and washed with $^1$N HCl (3×500 mL). The organic phase was separated, dried (MgSO$_4$), filtered, and concentrated under reduced pressure to leave a yellow syrup. The syrup was dissolved in DMF (6 mL) and purified by preparative HPLC (2 mL injection, C18 column 50% AcCN/H$_2$O, 30 mL/min) to give the product (2.4 g, 5.8 mmol, 82%) as a 1:2 mixture of cis:trans isomers. HPLC, MS both confirmed product.

EXAMPLE 5

Example 5 illustrates the coupling of pyridine to the acetyline moiety of the compound of Example 4.

Into an 8 mL vial was added the carboxylic acid (250 mg, 0.6 mmol), 3-iodopyridine (200 mg), dichlorobis (triphertylphosphine)palladium(II) (45 mg, 0.06 mmol), copper(I)iodide (49 mg, 0.26 mmol), NMP (4 mL) and DIEA (0.44 mL). The reaction was stirred at RT for 24 hours. The reaction mixture was filtered through a 0.2 micron PTFE filter and purified by preparative HPLC (2 mL injections, C18 column, 5–95% AcCN/H$_2$O over 60 minutes, 30 mL/min) to give the product (225 mg, 0.46 mmol, 76%) as a white solid. HPLC, MS, $^1$H NMR, $^{13}$C NMR all confirm product.

EXAMPLE 6

This example illustrates the derivatization of the carboxylic acid moiety of the compound of Example 5 with an amine.

Into a 20 mL vial was added the carboxylic acid (225 mg, 0.46 mmol), 3-ethoxy-4-methoxyphenethylarnine (102 μL, 0.55 mmol) in DMF (4 mL), DECP (90 μL, 0.55 mmol), and DIEA (240 μL, 0.55 mmol). The reaction was stirred at room temperature for 24 hours. HPLC analysis showed the reaction to be complete. The material was purified by preparative HPLC (2.25 mL injections, C18 column, isocratic 35% AcCN/H$_2$O, 30 mL/min) to give the cis enantiomers as a slightly yellow powder (AP20645, 61.9 mg, 0.092 mmol, 20%). HPLC, MS confirm product.

EXAMPLE 7

Example 7 illustrates the oxidation of the ring sulfur of a thiazolidinone compound of the invention.

Into a 4 mL vial was added the carboxylic acid (25 mg, 0.038 mmol), NMP (1 mL), and meta-chloroperbenzoic acid (46 mg). The reaction was heated at 60° C. for 24 hours. The material was purified by preparative HPLC (C18 column, 5% to 95% AcCN/H$_2$O over 40 minutes, 30 mL/min) to give the cis:trans enantiomers as a 1:1 mixture as a white powder (AF19470,12,2 mg, 0.0178 mmol, 47%). HPLC, MS confirmed product.

EXAMPLE 8

This example details the protocols utilized to assay the thiazolidinone library compounds for FSH antagonist activity.

CHO FSH-R 6CRE-luciferase cells were washed in DMEM/F12 without phenol red, resuspended at 2×10$^6$ cells per milliliter in DMEM/F12 without phenol red and dispensed into wells of a 96-well plate (50 microliters per well). Compounds were diluted in DMEM/F12 without phenol red to a final concentration of 4 times the desired assay concentration and dispensed into wells containing cells (25 microliters per well). After incubation for 30 minutes at 37° C., FSH (120 pM in DMEM/F12 without phenol red) was added in 25 microliters to generate a final assay concentration of 30 pM FSH. Plates were incubated at 37° C. for 4–6 hours. An equal volume of LucLite (Packard) was added and the plates were counted in a TopCount (Packard).

EXAMPLE 9

This example illustrates the procedure utilized to test whether the thiazolidinone compounds of the invention competed with FSH for binding to the FSH receptor.

a. Testing Compounds for Inhibition of Binding of $^{125}$I FSH to the Human FSH Receptor Expressed on the Surface of CHO Cells The human FSH receptor was cloned into the á-T8-12CA5-KH expression vector (Koller, et al., "A generic method for the production of cell lines expressing high levels of transmembrane receptors," *Analytical Biochem.* 250:51–60 (1997), which is incorporated herein by reference), and transfected into CHO cells. After G418 selection, cells were stained with FITC-labeled 12CA5 antibody and those expressing the FSH receptor were collected by FACS. Individual clones were expanded and examined for binding of $^{125}$I labeled FSH. CHO FSH-R clone 1H6 was expanded in a 15 liter spinner and membranes were prepared as described (Koller, et al., *Analytical Biochem.* 250 51–60 (1997)).

Individual compounds were examined for their inhibition of $^{125}$I FSH binding to these membranes as follows:

Mix:

50 μl membranes diluted in binding buffer (10 mM Tris pH 7.2, 1 mM MgCl$_2$, 1 mM CaCl$_7$ containing 0.1% BSA)—use amount of membranes to generate a 10:1 signal:noise 25 μl sample or buffer containing 4 μM unlabeled FSH (Cortex Biochem.)

25 μl $^{125}$I FSH (30,000 cpm per well)

Incubate for 2 hours at room temperature and filter onto pretreated GF/B Unifilter plates (blocked with 0.1% PEI for 30 minutes). Dry filter at 37° C., add 40 μl of Microscent 20 (Packard) and count using Packard TopCount.

b. Results

Membranes were prepared from chinese hamster ovary (CHO) cells which expressed FSH-R as described above. These cells specifically bind $^{125}$I-labeled FSH. When a binding assay was performed in the presence of 100 1M thiazolidinone, no inhibition of the radiolabeled FSH was observed. Thus, although the thiazolidinones are able to bind to the FSH receptor and to elicit a response, they do not block the interaction between FSH and its receptor.

EXAMPLE 10

This example illustrates a general procedure for library production by parallel synthesis on Rink Amide resin.

Step 1: Deprotection of Fmoc from Rink Amide Resin

Rink Amide Resin (loading: 0.53 mmol/g; 2.4 g, 1.272mmol) was treated with a solution of 20% piperidine in DMF (2×25 ml, 10 min for the first time and 20 min for the second time) to remove the Fmoc protecting group from the resin. The mixture was filtered and the resin was washed with DMF (3×25 ml), MeOH (3×25 ml), and CH$_2$Cl$_2$ (3×25 ml).

Step 2: Attachment of Various Fmoc-Protected Amino Acids to the Resin

The resin (1.272 mmol) was swollen in anhydrous DMF (10 ml). A solution of Fmoc-protected amino acid (2eq., 2.544 mmol), HOBT (389.2 mg, 2.544 mmol) and HBTU (964.2 mg, 2.544 mmol) in anhydrous DMF (15 ml) was added to the resin followed by adding DIEA (886.3□01, 5.088 mol). The mixture was shaked at room temperature on an orbital shaker overnight. The mixture was filtered and the resin was washed with DMF (3×25 ml), MeOH (3×25 ml), CH$_2$Cl$_2$ (3×25m1), and dried.

Step 3: Deprotection of Fmoc Group

The resin (1.272 mmol), prepared as described in step 2 above, was again treated with a solution of 20% piperidine in DMF (2×25 ml, 10 min for the first time and 20 min for the second time) to remove the Fmoc protecting group. The mixture was filtered and the resin was washed with DMF (3×25 ml), MeOH (3×25 ml), and CH$_2$Cl$_2$ (3×25 ml).

Step 4: Reaction with Various Aldehydes

The resin prepared above was distributed into a number of scintillation vials according to the number of different aldehydes to be used. To each amino acid on Rink Amide Resin (0.424 mmol) was added a solution of 10eq. of aldehyde (4.24mmol) and 20 eq. of mercaptosuccinic acid (1.27 g, 8.48mmol) in anhydrous THF (10 ml). The resulting reaction mixture was heated at 60° C. on the J-KEM block for 48 hr, the mixture was filtered, washed with THF (3×10 ml), MeOH (3×10ml), and CH$_2$Cl$_2$ (3×10 ml).

Step 5: Reaction with Various Amines

The resin again was distributed into 48 or 96 wells on a Robbins apparatus depending on the number of different amines to be used. To the resin-bound acid (0.027 mmol) was added a solution of HOBT (16.52 mg, 0.108 mmol) and HBTU (41 mg, 0.108 mmol) in anhydrous DMF (2 ml). DIEA(37.6□1, 0.216 mmol) was then added into each well followed by 10 eq. of amines(0.27 mmol). The reaction mixture was rotated at room temperature on an orbital shaker overnight. The mixture was then filtered and the resin was washed with DMF (3×2 ml), MeOH (3×2 ml), CH$_2$Cl$_2$ (3×2 ml), and dried.

Step 6: Cleavage from the Solid Support

The products were cleaved from the solid support for characterization according to the following procedure. To each well was added 95% TFA/DCM (2 ml). The resin was left standing for 1 h, and the solution were filtered into a 48 or 96 wells Robbins microtiter plate. The resin in each well was washed with dichloromethane (2 ml). The solutions were concentrated under a nitrogen stream and dried in Savant under vacuum. The compounds were purified by Gilson prep HPLC and the required fractions were concentrated in Savant. The final product was characterized by LC/MS. The structure for the libraries generated are shown in the following Table.

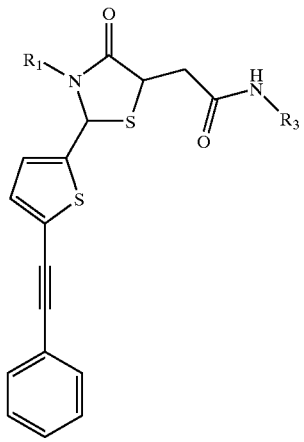

| Example 10 | R$_1$ | R$_3$ | LC@220 | (M + H)$^+$ |
|---|---|---|---|---|
| A1 | | | 5.49 min | 524 |
| B1 | | | 5.35 min | 538 |
| C1 | | | 5.34 min | 510 |

-continued
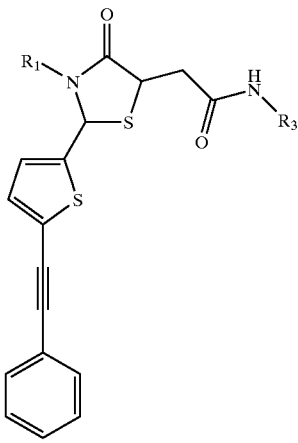
| Example 10 | R₁ | R₃ | LC@220 | (M + H)⁺ |
|---|---|---|---|---|
| D1 | H₂N-C(O)-CH₂-CH₂-CH(~)- | 4-Br-C₆H₄-CH₂-CH₂-(~) | 5.70 min | 597 |
| E1 | H₂N-C(O)-CH(CH₃)-(~) | 4-Br-C₆H₄-CH₂-CH₂-(~) | 5.87 min | 596 |
| F1 | H₂N-C(O)-CH(CH₂-C₆H₄-OH)-(~) | 4-Br-C₆H₄-CH₂-CH₂-(~) | 5.85 min, 5.96 min | 688 |
| G1 | H₂N-C(O)-CH(CH₂CH₂COOH)-(~) | 4-Br-C₆H₄-CH₂-CH₂-(~) | 5.53 min, 5.64 min | 654 |
| H1 | H₂N-C(O)-CH(CH₂-C(O)-NH₂)-(~) | 4-Br-C₆H₄-CH₂-CH₂-(~) | 5.38 min | 639 |
| I1 | H₂N-C(O)-CH₂-CH₂-CH₂-CH(~)- | 4-Br-C₆H₄-CH₂-CH₂-(~) | 5.74 min | 610 |
| J1 | H₂N-C(O)-CH₂-(~) | 4-Br-C₆H₄-CH₂-CH₂-(~) | 5.74 min | 582 |

-continued
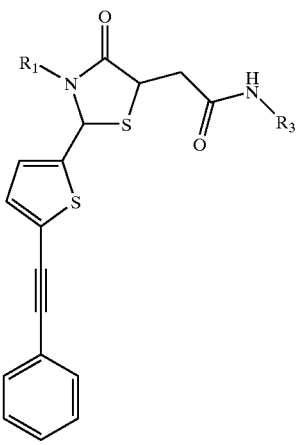
| Example 10 | R₁ | R₃ | LC@220 | (M + H)⁺ |
|---|---|---|---|---|
| K1 | 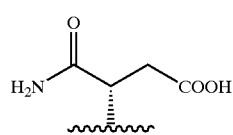 | 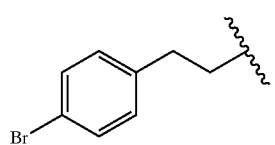 | 5.54 min<br>5.65 min | 640 |
| L1 | 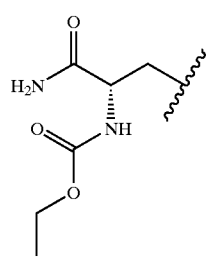 | 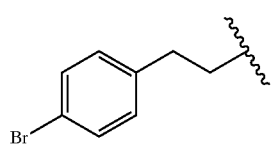 | 5.88 min | 683 |
| M1 | 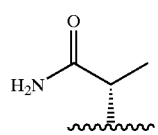 | 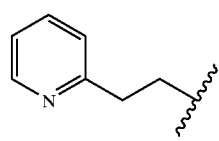 | 4.17 min | 519 |
| N1 | 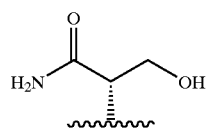 | 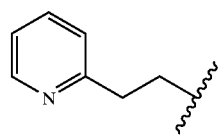 | 3.97 min | 535 |
| O1 | 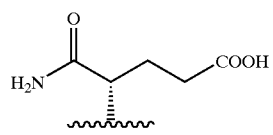 | 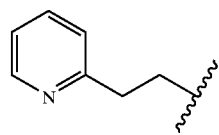 | 4.00 min | 577 |
| P1 | 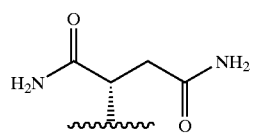 | 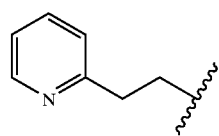 | 3.99 min | 562 |

-continued
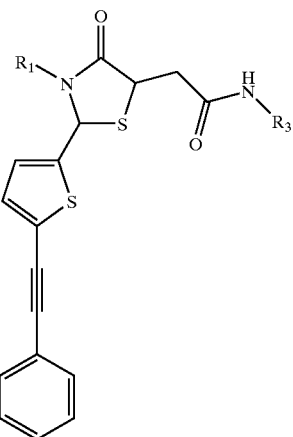
| Example 10 | R₁ | R₃ | LC@220 | (M + H)⁺ |
|---|---|---|---|---|
| Q1 | H₂N-C(O)-(CH₂)₃- | pyridin-2-yl-CH₂- | 4.11 min | 533 |
| R1 | H₂N-C(O)-CH(CH₂COOH)- | pyridin-2-yl-CH₂- | 3.97 min / 4.08 min | 563 |
| S1 | H₂N-C(O)-(CH₂)₂- | 3,4-dimethoxyphenyl-CH₂- | 5.08 min | 578 |
| T1 | H₂N-C(O)-CH(CH₃)- | 3,4-dimethoxyphenyl-CH₂- | 5.24 min | 578 |
| U1 | H₂N-C(O)-CH(CH₂OH)- | 3,4-dimethoxyphenyl-CH₂- | 4.92 min / 5.05 min | 594 |
| V1 | H₂N-C(O)-CH(CH₂C(O)NH₂)- | 3,4-dimethoxyphenyl-CH₂- | 4.73 min / 4.81 min | 621 |

-continued
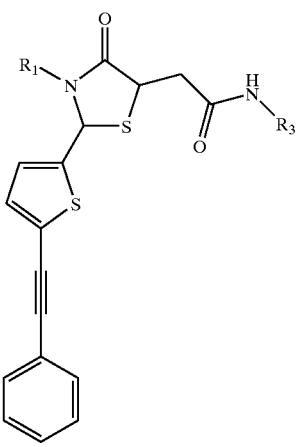
| Example 10 | R₁ | R₃ | LC@220 | (M + H)⁺ |
|---|---|---|---|---|
| W1 | 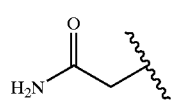 | 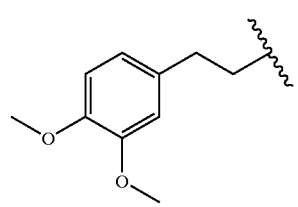 | 5.04 min | 564 |
| X1 | 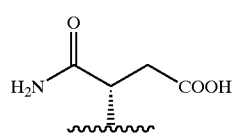 | 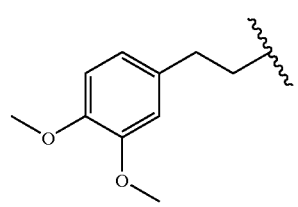 | 4.86 min<br>4.96 min | 622 |
| Y1 | 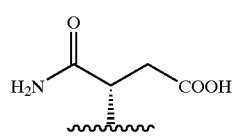 | 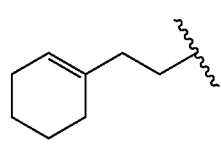 | 4.74 min | 566 |
| Z1 | 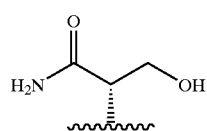 | 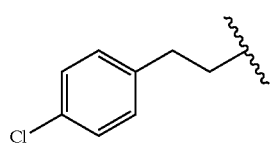 | 5.48 min<br>5.55 min | 568 |
| A2 | 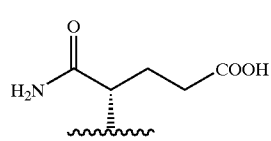 | 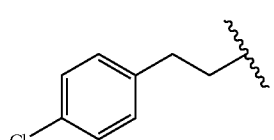 | 5.47 min | 610 |
| B2 | 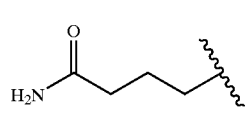 | 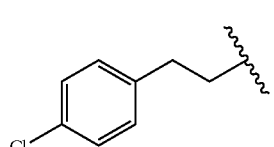 | 5.60 min | 566 |

-continued

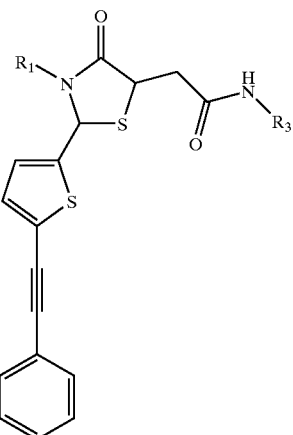

| Example 10 | R₁ | R₃ | LC@220 | (M + H)⁺ |
|---|---|---|---|---|
| C2 | H₂N-C(O)-phenyl- (3-carbamoyl-phenyl) | 4-chlorobenzyl-CH₂- | 4.31 min / 4.42 min | 599 |
| D2 | H₂N-C(O)-CH₂-CH₂- | 4-chlorobenzyl-CH₂- | 5.59 min | 538 |
| E2 | H₂N-C(O)-CH(CH₂OH)- | imidazol-4-yl-CH₂-CH₂- | 3.86 min / 3.90 min | 524 |
| F2 | H₂N-C(O)-CH(CH₂CH₂COOH)- | imidazol-4-yl-CH₂-CH₂- | 3.91 min | 566 |
| G2 | H₂N-C(O)-CH(CH₂COOH)- | imidazol-4-yl-CH₂-CH₂- | 3.90 min / 4.00 min | 552 |

EXAMPLE 11

Preparation of [3-(2-Carbamoyl-ethyl)-4-oxo-2-(5-phenylethynyl-thiophen-2-yl)-thiazolidin-5-yl]-acetic acid.

A mixture of β-alanine amide hydrochloride (3.11 g, 25 mmol), 5-(phenylethynyl)thiophene-2-carboxaldehyde (5.31 g, 25 mmol), mercaptosuccinic acid (11.26 g, 75 mmol) and diisopropylethylamine (3.6 g, 27.5 mmol) was stirred in acetonitrile (300 mL) at reflux for forty eight hours. The solvent was evaporated and the residue was shaken with 2 N HCl (500 mL) and ethyl acetate (3×200 mL) The ethyl acetate solution was washed with water then brine and dried (MgSO₄) and evaporated. The product was purified on a 600 mL. silica dry column by elution with dichloromethane:acetic acid (99:1) followed by dichloromethane:methanol:acetic acid (95:5:1). The appropriate fractions were evaporated. The residue was washed with ether and dried to provide the title compound as a white solid: (2.44 g, 23.5%): m.p. 175–178. $^1$H-NMR (DMSO-d₆) δ 12.6 (broad, 1H), 7.56–7.57 (d, 1H, J=2.4 Hz), 7.54–7.55 (d, 1H, J=3.6 Hz), 7.4–7.46 (m, 4H), 7.28–7.32 (m, 2H), 6.90(s, 1H), 6.15 (s, 0.5 H), 6.12–6.13 (d, 0.5H, J=1.6 Hz), 4.24–4.28 (m, 1H), 4.15–4.19 (dd, 0.5H, J=3.6 Hz), 2.97–3.09 (m, 1H), 2.64–2.74 (m, 1H), 2.36–2.46 (m, 1H), 2.08–2.21 (m, 1H); MS(ESI) 413[M-H], 415[M+H]. Analytical HPLC; Capcell Pak C18, 30% acetonitrile: 70% 0.1% aqueous TFA.51 trans: 49 cis. FTIR (ATR) 1650, 1720 cm⁻¹. Anal. ($C_{20}H_{18}N_2O_4S_2$) calc. C, 57.95; H, 4.38; N, 6.76. obs. C, 57.59; H, 4.34; N, 6.56.

EXAMPLE 12

Preparation of 3-[(2S*,5R*)-5-{[2-(1H-Indol-3-yl)-ethylcarbamoyl]-methyl}-4-oxo-2-(5-phenylethynyl-thiophen-2-yl)-thiazolidin-3-yl]-propionamide A mixture of [3-(2-carbamoyl-ethyl)-4-oxo-2-(5-phenylethynyl-thiophen-2-yl)-thiazolidin-5-yl]-acetic acid (1.36 g,3.28 mmol), 3-indolylethylamine (0.77 g, 4.8 mmol), diethyl cyanophosphonate (0.781 g, 4.8 mmol) and diisopropylethylamine (0.62 g, 4.8 mmol) was stirred in DMF (50 mL) for three hours at room temperature. The mixture was poured into water (100 mL). The product was extracted into ethyl acetate (2×100 mL). The extract was washed successively with sat. NaHCO$_3$, H$_2$O, brine, and then dried (MgSO$_4$). The solvent was evaporated to a brown gum, which was washed twice with methanol to remove the dark color to provide the title compound as an off-white solid (0.3 g, 16.8%). $^1$H NMR (DMSO-d$_6$) δ 10.8 (s, 1H), 8.19–8.23 (t, 1H), 7.51–7.55 (m, 3H), 7.33–7.46 (m, 4H), 7.27–7.31 (m, 3H), 7.14–7.15 (d, 1H, J=2.2 Hz), 7.02–7.07 (t, 1H), 6.91–6.98 (m, 2H), 6.13 (s, 1H ), 4.15–4.20 (dd, 1H, J=3.1 Hz ), 3.55–3.64 (m, 1H), 3.27–3.41 (m, 2H), 2.97–3.07 (m, 2H), 2.79–2.84 (t, 2H), 2.60 (s, 1H), 2.55–2.56 (d, 1H, J=4.7 Hz), 2.35–2.45 (m,1H), 2.08–2.18 (m, 1H), 95% cis based on peaks at δ 6.13 and 4.15–4.20); MS(ESI)557[M+H]$^+$.FTIR(ATR) 1620, 1660 cm$^{-1}$.Anal. (C$_{30}$H$_{28}$N$_4$O$_3$S$_2$) calc. C, 64.72; H, 5.07; N, 10.06. Obs. C, 64.55; H, 4.98; N, 9.93.

EXAMPLE 13

Preparation of 3-[(2S*,5R*)-5-{[2-(4-Bromo-phenyl)-ethylcarbamoyl]-methyl}-4-oxo-2-(5-phenylethynyl-thiophen-2-yl)-thiazolidin-3-yl]-propionamide.

A mixture 3-(3-amino-3-oxopropyl)-4-oxo-2-(5-(2-phenylethynyl)thien-2-yl)-1,3-thiazolidin-5-yl)acetic acid (1.36 g,3.2 mmol), 4-bromophenethylamine (1.35 g, 4.8 mmol), diethyl cyanophosphonate (0.782 g, 4.8 mmol ) and diisopropylethylamine (1.24 g, 9.6 mmol) was stirred in DMF (50 mL) for three hours at room temperature under a nitrogen atmosphere. The mixture was poured into 1 N HCl (100 mL). The product was extracted into ethyl acetate (3×100 mL). The ethyl acetate extract was washed successively with 1 N HCl, H$_2$O, sat. NaHCO$_3$ and brine, and then dried (MgSO$_4$). The ethyl acetate solution was evaporated to a gum (0.9 g), which contained very little product when tested by $^1$H NMR. The MgSO$_4$ was stirred in water (2 L) and filtered. The insoluble white powder was washed with water several times and air-dried on the filter overnight to provide the title compound as a white solid: (0.9 g, 47%). m.p.224–227°. $^1$H NMR (DMSO-d$_6$) δ 8.10–8.17 (m, 1H), 7.52–7.55 (m, 2H), 7.41–7.48 (m, 6H), 7.25–7.32 (m, 2H), 7.15–7.19 (m, 2H), 6.9 (s, 1H), 6.12 )s, 0.66 H, cis), 6.07 (d, 0.33 H trans), 4.21–4.23 (m, 0.33 H trans), 4.12–4.17 (dd, 0.65 H, J=3.3 Hz cis), 3.50–3.63 (m, 1H), 3.19–3.30 (m, 2H), 2.91–3.06(m, 2H), 2.54–2.70 (m, 3H, 2.35–2.47 (m, 1H), 2.10–2.17 (m, 1H); MS(ESI) [M+H]$^+$596/598 (1 Br pattern). FRIR(ATR) 1650, 1670 cm$^{-1}$.Anal.HPLC: Metacapsil C18, 1:1 acetonitrile:water. Ret.Time (mins.) 15.1(cis, 66%), 17.8 (trans, 33%). The cis isomer crystallized from hot ethyl acetate on cooling.m.p.241–243°. $^1$H NMR (DMSO-d$_6$) δ 6.12 (s, 1H), 4.12–4.17 (dd, 1H). Anal. (C$_{28}$H$_{26}$BrN$_3$O$_3$S$_2$ 2H$_2$O) Calc, C, 53.16; H, 4.78; N, 6.64. Obs. C, 53.16; H, 4.30; N, 6.64.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed:

1. A compound of the formula

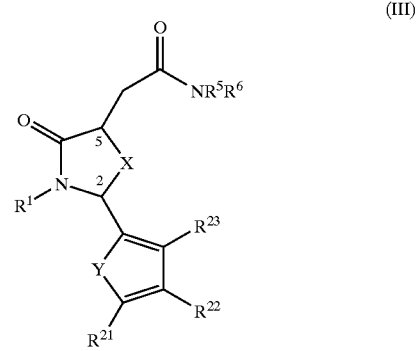

(III)

wherein, $R^1$ is selected from the group consisting of aryl, substituted aryl, alkyl and substituted alkyl;

$R^{21}$, $R^{22}$, and $R^{23}$ are independently selected from the group consisting of H, halogen, lower alkyl, substituted lower alkyl, lower alkoxy, substituted lower alkoxy, phenyl, substituted phenyl, aryloxy, substituted aryloxy, alkynyl, substituted alkynyl and nitro;

Y is selected from the group consisting of O, S and NR$^{24}$, wherein R$^{24}$ is H or lower alkyl;

$R^5$ and $R^6$ are independently selected from the group consisting of hydrogen, alkyl, substituted alkyl, cycloalkyl, substituted cycloalkyl, arylalkyl, substituted arylalkyl, heterocyclicalkyl and substituted heterocyclicalkyl; and X is a member selected from the group consisting of S, S=O, and O=S=O.

2. The compound according to claim 1, wherein $R^{21}$, $R^{22}$ and $R^{23}$ are independently selected from the group consisting of hydrogen and a moiety of Formula (VIII):

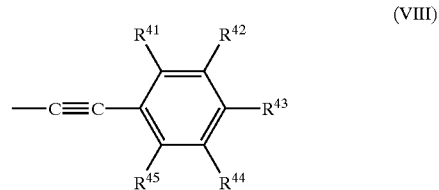

(VIII)

wherein $R^{41}$, $R^{42}$, $R^{43}$, $R^{44}$ and $R^{45}$ are independently selected from the group consisting of hydrogen, halogen, nitro and trifluoromethyl.

3. The compound according to claim 2, wherein said compound is selected from the group consisting of 37
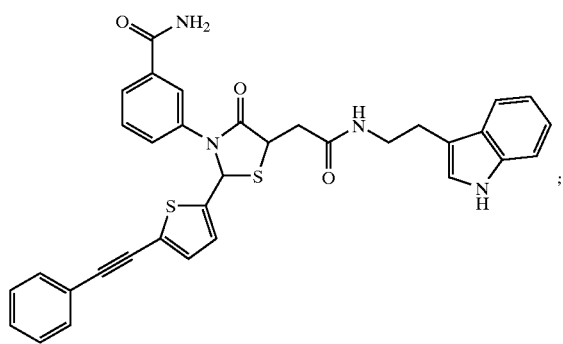
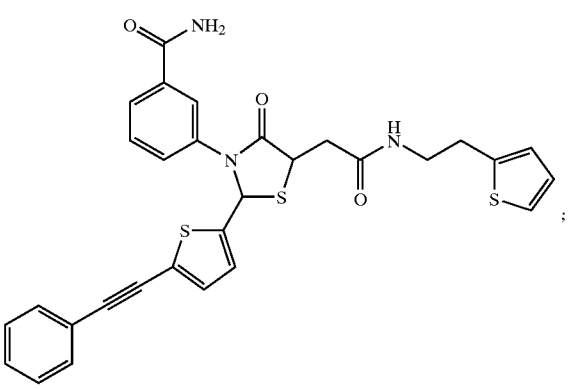
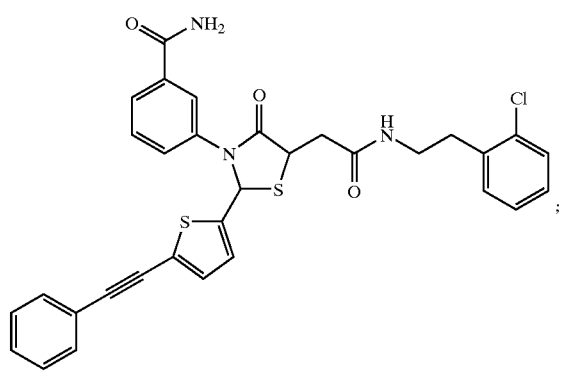
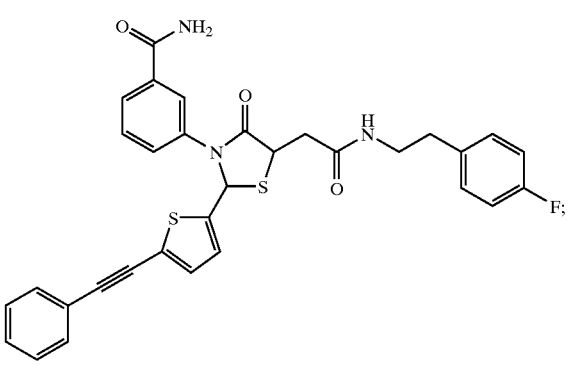
38
-continued
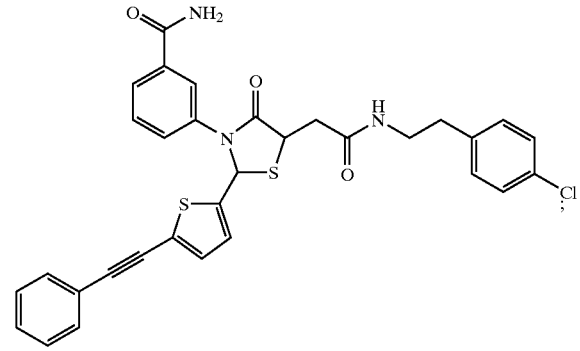
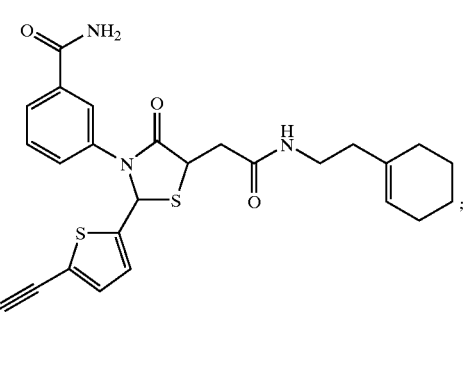
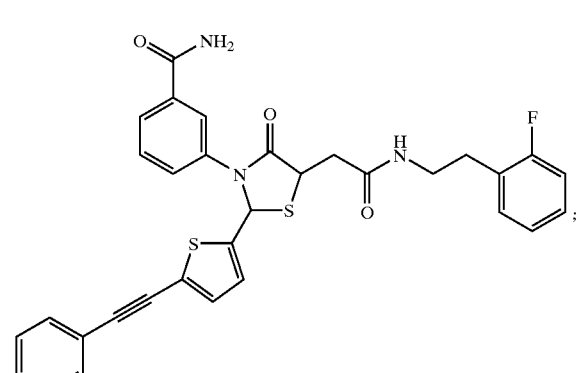

-continued
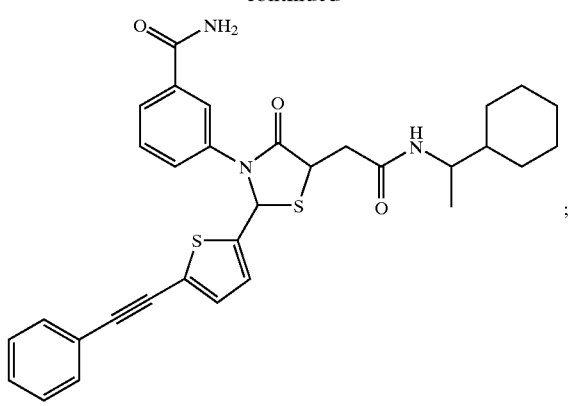
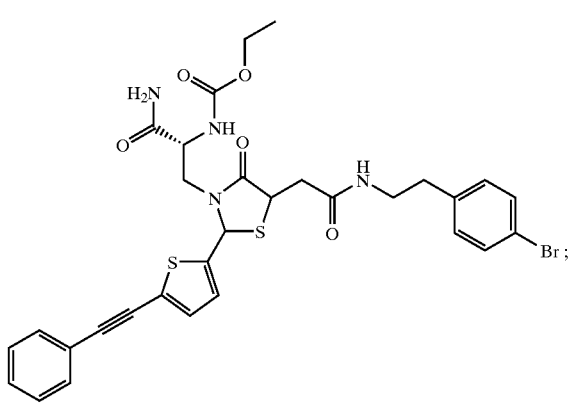
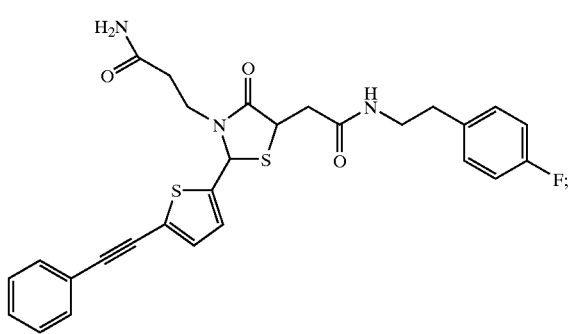
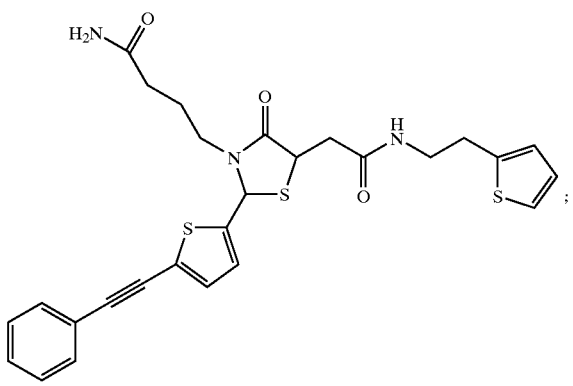
-continued
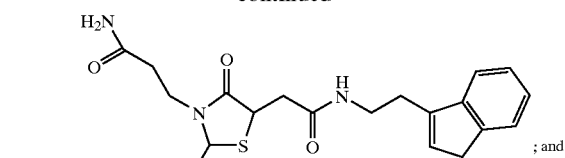
; and
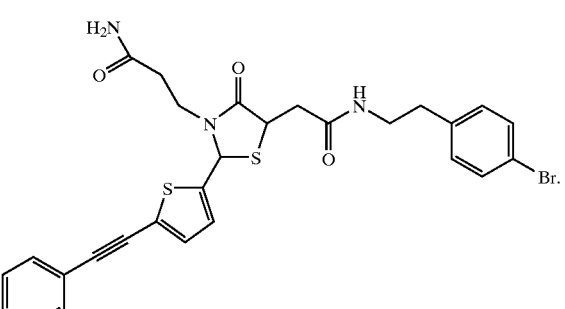
4. The compound of claim 2 having the structure
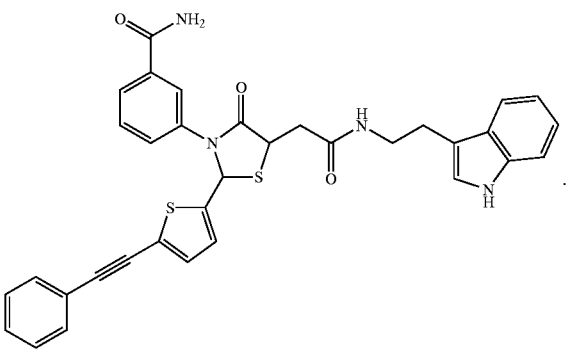
5. The compound of claim 2 having the structure
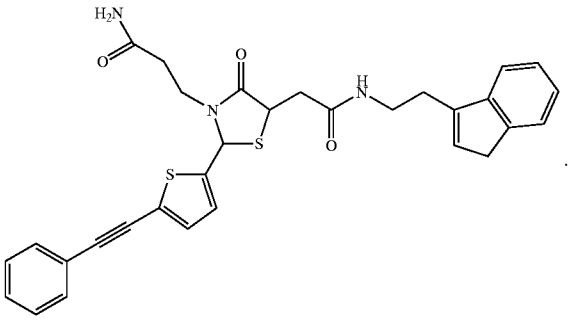

6. The compound according to claim 1, wherein said compound has a FSH antagonizing activity as expressed by an $IC_{50}$ standard of no more than 11 μM.

7. A method of antagonizing a FSH receptor comprising: contacting a cell comprising said FSH receptor with a compound of claim 1.

8. A method of inhibiting follicle maturation comprising: contacting a follicle cell comprising a FSH receptor with an effective amount of a compound of claim 1.

9. A method for inhibiting ovulation comprising: contacting an ovulation cell comprising a FSH receptor with an effective amount of a compound of claim 1.

10. A method of contraception comprising administering to a subject an effective amount of a compound of claim 1.

11. A method for treating endometriosis in a subject comprising: administering to said subject an effective amount of a compound of claim 1.

12. A method for treating endocrine hormone-dependent tumors in a subject comprising: administering to said subject an effective amount of a compound of claim 1.

13. A method for treating uterine fibroids in a subject comprising: administering to said subject an effective amount of a compound of claim 1.

* * * * *